(12) United States Patent
Hörsting et al.

(10) Patent No.: US 12,201,739 B2
(45) Date of Patent: Jan. 21, 2025

(54) METHOD FOR AVOIDING THE MICROBIAL ATTACK OF A CLEANING APPARATUS FOR A METERING UNIT, AND CLEANING APPARATUS

(71) Applicant: Brillux GmbH & Co. KG, Münster (DE)

(72) Inventors: Ingo Hörsting, Drensteinfurt (DE); Dietmar Erber, Münster (DE); Rainer Storb, Nottuln (DE); Sven Fels, Münster (DE)

(73) Assignee: BRILLUX GMBH & CO. KG, Münster (DE)

( * ) Notice: Subject to any disclaimer, the term of this patent is extended or adjusted under 35 U.S.C. 154(b) by 19 days.

(21) Appl. No.: 17/430,029

(22) PCT Filed: Feb. 11, 2020

(86) PCT No.: PCT/EP2020/053385
§ 371 (c)(1),
(2) Date: Mar. 3, 2022

(87) PCT Pub. No.: WO2020/165118
PCT Pub. Date: Aug. 20, 2020

(65) Prior Publication Data
US 2022/0184257 A1    Jun. 16, 2022

(30) Foreign Application Priority Data
Feb. 11, 2019    (DE) .......................... 102019103273.3

(51) Int. Cl.
*A61L 2/20*    (2006.01)
*A61L 2/22*    (2006.01)
(Continued)

(52) U.S. Cl.
CPC ................. *A61L 2/202* (2013.01); *A61L 2/22* (2013.01); *B01F 33/841* (2022.01);
(Continued)

(58) Field of Classification Search
None
See application file for complete search history.

(56) References Cited

U.S. PATENT DOCUMENTS 2,323,550 A    7/1943  Lukens
2,713,545 A    7/1955  Kather
(Continued)

FOREIGN PATENT DOCUMENTS

AU    617422    11/1991
CH    618462    7/1980
(Continued)

OTHER PUBLICATIONS

Google Patents translation of DE10248561A1 (Year: 2023).*
(Continued)

*Primary Examiner* — Eric W Golightly
(74) *Attorney, Agent, or Firm* — Honigman LLP; Andrew N. Weber; Jonathan P. O'Brien (57) ABSTRACT

What is presented and described is a method for avoiding the microbial attack of a cleaning apparatus, in particular a cleaning apparatus for a metering system, wherein the cleaning apparatus has at least one mechanical cleaning element with at least one cleaning surface, wherein the method is characterized in that the at least one cleaning surface of the at least one mechanical cleaning element is exposed, at least temporarily, to an oxidizing agent. The present invention further relates to a method for cleaning a metering system, in particular for a dispersion, especially a paint-metering system, to a cleaning apparatus, and to a metering system.

6 Claims, 6 Drawing Sheets

(51) Int. Cl.
*B01F 33/841* (2022.01)
*B01F 35/10* (2022.01)
*B01F 35/12* (2022.01)
*B08B 1/12* (2024.01)
*B08B 1/32* (2024.01)
*B08B 1/50* (2024.01)
*B01F 101/30* (2022.01)

(52) U.S. Cl.
CPC .......... *B01F 35/121* (2022.01); *B01F 35/146* (2022.01); *B08B 1/12* (2024.01); *B08B 1/32* (2024.01); *B08B 1/50* (2024.01); *A61L 2202/17* (2013.01); *B01F 2101/30* (2022.01)

(56) References Cited

U.S. PATENT DOCUMENTS

| | | | |
|---|---|---|---|
| 3,574,651 | A | 4/1971 | Nitzsche et al. |
| 3,895,956 | A | 7/1975 | Yoshida et al. |
| 3,923,704 | A | 12/1975 | Gunning et al. |
| 4,063,958 | A | 12/1977 | Roth et al. |
| 4,125,673 | A | 11/1978 | Roth et al. |
| 4,137,380 | A | 1/1979 | Gunning et al. |
| 5,356,463 | A | 10/1994 | Kober et al. |
| 5,584,921 | A | 12/1996 | Wagner et al. |
| 5,998,525 | A | 12/1999 | Wang et al. |
| 6,036,581 | A * | 3/2000 | Aoki ................ B24C 3/18 451/39 |
| 6,468,336 | B1 | 10/2002 | Fiedler et al. |
| 6,638,353 | B1 | 10/2003 | Rathschlag et al. |
| 7,789,959 | B2 | 9/2010 | Fichtner et al. |
| 9,334,196 | B2 | 5/2016 | Connors, Jr. et al. |
| 2005/0150417 | A1 | 7/2005 | Hirsbrunner et al. |
| 2006/0174922 | A1 | 8/2006 | Mader |
| 2009/0211491 | A1 | 8/2009 | Ogata et al. |
| 2010/0119850 | A1 | 5/2010 | Browne et al. |
| 2013/0145966 | A1 | 6/2013 | Schildbach et al. |
| 2013/0170014 | A1 | 7/2013 | Kong et al. |
| 2019/0048214 | A1 | 2/2019 | Hörsting et al. |

FOREIGN PATENT DOCUMENTS

| | | | | |
|---|---|---|---|---|
| DE | 1031910 | | 6/1958 | |
| DE | 2745853 B | * | 2/1979 | ........ B01F 15/00019 |
| DE | 4424685 | | 1/1996 | |
| DE | 10248561 A1 | * | 4/2004 | ................ A01J 7/02 |
| DE | 102014013455 | | 3/2016 | |
| DE | 202014011090 | | 11/2017 | |
| DE | 202017107111 | | 8/2018 | |
| EP | 2745853 | | 2/1979 | |
| EP | 1297079 | | 2/2003 | |
| EP | 1541225 | | 6/2005 | |
| EP | 1259572 | | 7/2005 | |
| EP | 1990102 | | 11/2008 | |
| EP | 2243808 | | 10/2010 | |
| EP | 2351590 | | 8/2011 | |
| GB | 2121424 | | 12/1983 | |
| GB | 2292695 | | 3/1996 | |
| JP | 47-013184 | | 7/1972 | |
| JP | H04107824 | | 4/1992 | |
| JP | H04107824 A | * | 4/1992 | |
| JP | 07-278463 | | 10/1995 | |
| JP | 2005-139320 | | 6/2002 | |
| JP | 2005-336357 | | 12/2005 | |
| JP | 2007167837 A | | 7/2007 | |
| JP | 4562388 | | 10/2010 | |
| JP | 2011-079908 | | 4/2011 | |
| RU | 2142975 | | 12/1999 | |
| WO | 200068324 | | 11/2000 | |
| WO | 2001/048098 | | 7/2001 | |
| WO | 2004034775 | | 4/2004 | |
| WO | 2005073257 | | 8/2005 | |
| WO | 2007080612 | | 7/2007 | |
| WO | 2017144694 | | 8/2017 | |
| WO | 2020/165118 | | 8/2020 | |
| WO | 2020/212622 | | 10/2020 | |

OTHER PUBLICATIONS

Translation of JPH04107824A retrieved from PE2E (Year: 2023).*
International Search Report from PCT/EP2020/053385 mailed Jun. 17, 2020 2 pages.
International Preliminary Report on Patentability for PCT/EP2017/054386 Mailed TBD, 11 pages.
International Search Report for PCT/EP2017/054386 Mailed May 15, 2017, 3 pages.
Written Opinion of the International Searching Authority for PCT/EP2017/054386 Mailed May 15, 2017, 7 [ages.
International Search Report for PCT/EP2020/060993, 3 pages.
International Preliminary Report on Patentability for PCT/EP2020/060993, 8 pages.
European Office Action, Application No. 207058983, dated Sep. 12, 2023, 6 pages, not in English.

* cited by examiner

METHOD FOR AVOIDING THE MICROBIAL ATTACK OF A CLEANING APPARATUS FOR A METERING UNIT, AND CLEANING APPARATUS

CROSS-REFERENCE TO RELATED APPLICATIONS

This application is a national stage application under 35 U.S.C. § 371 of International Application No. PCT/EP2020/053385, filed Feb. 11, 2020, which claims the benefit of German Patent Document DE 102019103273.3, filed Feb. 11, 2019. The entire contents of each of these applications is hereby incorporated by reference herein.

FIELD OF THE INVENTION

The invention relates to a method for avoiding the microbial attack of a cleaning apparatus, in particular a cleaning apparatus for a metering system, the cleaning apparatus having at least one mechanical cleaning element with at least one cleaning surface. The invention also relates to a method for cleaning a metering system, a cleaning apparatus, and a metering system.

BACKGROUND OF THE INVENTION

Metering systems enable the precise provision of a certain amount of a dispersion upon demand. For the purposes of the present invention, metering systems basically mean all systems that enable a metered supply of a material. Metering systems are used, in particular, when mixing dispersion paints.

A metering system for paints is described, for example, in DE 196 54 829 A1. A particular problem with metering systems for dispersions is their microbial attack by fungi and bacteria. This is due to the storage of the dispersion(s) in a corresponding container in the metering system, sometimes for several weeks and months. The microbial attack is not limited to the storage container in the metering system, but spreads to all elements of the metering system that come into contact with the contaminated dispersion, particularly also to the metering unit, by means of which the stored dispersion can be dispensed in a controlled amount. The metering unit usually comprises a so-called pump head, via which the dispersion can be dispensed from the metering system. Over time, the pump head and, in particular, its outlet opening or nozzle become clogged with dispersion residue, so that regular, usually mechanical cleaning of this outlet opening is necessary. For this purpose, cleaning apparatuses are known in practice which comprise, for example, a rotating brush, with the aid of which the outlet opening is reliably cleaned. When the cleaning apparatus is in operation, the rotating brush, in turn, is cleaned or rinsed in a cleaning bath, in which it is partially immersed during the cleaning operation. If the cleaning bath is not changed regularly, fungi and bacteria can form which contaminate the cleaning apparatus. If the metering system has a plurality of storage containers for dispersions with a correspondingly plurality of pump heads, as is the case, for example, in paint mixing systems, the microbial attack of a stored dispersion can also spread to the other dispersions. This can occur when the contaminated dispersion residue is cleaned off at the outlet opening or nozzle of a pump head and then collects in the cleaning bath. The microbial attack then spreads to the pump heads of the initially unaffected dispersions via the cleaning brush, which is then continually rinsed in the cleaning bath.

SUMMARY OF THE INVENTION

The present invention is therefore based on the object of specifying a method by means of which the microbial attack of a cleaning apparatus is effectively avoided, in particular the microbial attack of a cleaning apparatus for a metering system.

Another object of the present invention is to provide a cleaning apparatus for a metering system, in particular for a dispersion, especially for a paint-metering system, in which the microbial attack of the cleaning apparatus and of the metering system is effectively avoided.

Further objects result from the following statements.

In terms of the method, the above objects are achieved with a method according to the preamble of claim 1 in that the at least one cleaning surface of the at least one mechanical cleaning element is at least temporarily exposed to an oxidizing agent.

The particular advantage of the method according to the invention is that the application of an oxidizing agent to the at least one mechanical cleaning element effectively prevents the accumulation and subsequent propagation of a microbial attack, e.g. bacteria, mold, or yeast, over a long period of time. If a microbial attack has already started, the method according to the invention enables it to be reliably eliminated.

Surprisingly, it has been shown that with the method according to the invention for avoiding the microbial attack of a cleaning apparatus in a metering system, especially a paint-metering system, paint dispersions stored there can be protected from microbial attack for months, since on the one hand, as mentioned, the accumulation and a subsequent propagation of a microbial attack in the cleaning apparatus itself is effectively avoided and, in connection therewith, a spread of the microbial attack, insofar as it already exists, is avoided in the components to be cleaned with the cleaning apparatus. According to the invention, this is achieved by consistently applying the oxidizing agent to the mechanical cleaning element or elements of the cleaning apparatus. A dispersion stored in the metering system can be free of preservatives and will still have long-lasting protection against a microbial attack. Even with frequent use of the metering system and repeated filling of the container with fresh dispersion, protection against fungal and bacterial attack is ensured by the method according to the invention with regular cleaning.

The application of the at least one cleaning surface of the at least one cleaning element of the cleaning apparatus can take place continuously or discontinuously, for example at periodic intervals (for example every 6, 12, or 24 hours). This is determined, among other things, by the ambient conditions (temperature, air humidity, etc.) in which the cleaning apparatus is used and which may favor the formation or propagation of a microbial attack.

In principle, very different oxidizing agents are suitable for preventing or eliminating a microbial attack. Oxidizing agents that are gaseous, liquid, or solid are possible. Liquid and solid oxidizing agents are preferably used as aqueous solutions, as this simplifies handling. The oxidizing agent is thus preferably an oxidizing fluid. Gaseous oxidizing fluids have also proven to be particularly suitable.

In order to achieve the most thorough and complete application of the at least one cleaning surface of the at least one cleaning element, an advantageous embodiment of the invention provides that the oxidizing agent is sprayed or blown onto the at least one mechanical cleaning surface. In addition, it is preferred that the oxidizing agent is sprayed or blown onto the at least one mechanical cleaning surface essentially along its longitudinal extension, preferably over the entire surface This ensures that there are no untreated surface sections where the microbial attack can start when the material is exposed.

With regard to the chemical composition, a wide range of oxidizing agents is available. The oxidizing agent is advantageously an oxygen- or chlorine-based oxidizing agent or a mixture thereof, preferably an oxygen-based oxidizing agent. The oxidizing agent is preferably selected from the group consisting of sodium hypochlorite, potassium hypochlorite, Javel water, chlorine, ozone, hydrogen peroxide, peroxyacetic acid, perborate, percarbonate, and mixtures thereof. These oxidizing agents are strong oxidizing agents that effectively suppress the growth of microbial organisms.

The oxidizing agent is particularly preferably selected from the group consisting of sodium hypochlorite, hydrogen peroxide, ozone, and mixtures thereof. The oxidizing agents from the group mentioned have proven to be particularly suitable for protecting the dispersion from microbial attack, since they are effective oxidizing agents. Furthermore, these oxidizing agents are essentially unproblematic, particularly in the amounts expediently provided for the dispersion. With the amounts expediently provided, the aforementioned oxidizing agents particularly do not cause a noticeable change in the color and/or quality of the dispersion.

As mentioned, the use of an oxidizing fluid, i.e. a gaseous or liquid oxidizing agent, is preferred. A gaseous oxidizing agent has proven to be particularly suitable. According to a particularly preferred embodiment of the invention, the oxidizing agent contains ozone. If the oxidizing agent contains ozone or if ozone is used as an oxidizing agent, there is a particularly long-lasting antimicrobial effect. If the cleaning apparatus is used in connection with a metering system for dispersions, it turns out to be an advantage that ozone is compatible with the common constituents of dispersions, in particular the common constituents of dispersion paints or pigment pastes. In addition, ozone can be produced very easily at the point of use.

Ozone can be generated, for example, from a chemical reaction of potassium permanganate with concentrated sulfuric acid or from the electrolysis of diluted sulfuric acid, particularly at low temperatures. Ozone can also be generated from air or oxygen under the effects of UV radiation.

According to a preferred embodiment of the method according to the invention, the ozone is generated starting from air, in particular dried air, oxygen, or an oxygen mixture with argon or carbon dioxide, in an ozone generator comprising a voltage source, in particular a high-voltage generator, and a discharge unit. The design of common ozone generators is known from the prior art. According to a common variant of ozone production, oxygen molecules are dissociated into oxygen atoms in a discharge unit, preferably by silent electrical discharge, so-called "corona discharge," according to which ozone synthesis and ozone enrichment take place in the plasma of the discharge filaments. The resulting proportion of ozone in the final concentration of the gas mixture can be 1 to 5% by weight with air as the starting gas and 6 to 13% by weight with oxygen as the starting gas. Air is preferably used as the starting gas for generating ozone. When the ozone is generated in a generator, ozone is thus produced in a clean manner starting from inexpensive starting materials.

According to a particularly advantageous embodiment of the invention, the at least one cleaning surface of the at least one mechanical cleaning element is cleaned, at least temporarily, in a cleaning bath during operation of the cleaning apparatus, the oxidizing agent optionally also acting on the cleaning bath at least temporarily.

In this embodiment of the cleaning apparatus, the at least one cleaning surface of the at least one mechanical cleaning element itself is cleaned, so that the microbial contaminants adhering to the at least one cleaning surface are washed off the cleaning surface. As a result, the cleaning apparatus can operate completely independently over a longer period of time. Since the microbial attack thus reaches the cleaning bath from the cleaning surface, it can make sense that the cleaning bath itself is exposed to the oxidizing agent at least temporarily, in addition to the cleaning surface. In this case, the microbial attack can be combated even more effectively, since the residue of the microbial attack is combated directly in the cleaning bath.

According to a further advantageous embodiment of the invention, the oxidizing agent is sprayed or blown onto the at least one cleaning surface of the at least one mechanical cleaning element outside the cleaning bath. As a result, the oxidizing agent can be directed even more specifically to the at least one cleaning surface.

According to the invention, the mechanical cleaning element of the cleaning apparatus has at least one cleaning surface. This surface can be designed in different ways. A circumferential cleaning surface is preferred, in particular in the case of a cylindrical design of the mechanical cleaning element. It goes without saying that elliptical or polygonal surface areas are also possible instead of a cylindrical design with a circular surface area. Instead of a circumferential cleaning surface, several cleaning surfaces that are not connected to one another are also possible, for example a plurality of essentially flat cleaning surfaces, which can be arranged, for example, pointing radially outward and rotating about a common axis.

When designing the at least one cleaning surface, it must be taken into account that, in principle, all mechanical cleaning techniques can be used within the scope of the present invention, such as wiping, scrubbing, grinding, etc. The cleaning surface is designed accordingly, for example as a brush or sponge, based on the cleaning technique selected. According to an advantageous embodiment of the invention, the at least one cleaning element is designed as a brush and its cleaning surface is designed accordingly as a brush surface. The design as a cylindrical or roller-shaped brush is particularly preferred. Regardless of the geometric design of the brush surface, the oxidizing agent is preferably sprayed or blown into the brush essentially parallel to the bristles, so that the bristles can be cleaned of a microbial attack along their entire length, which leads to a particularly thorough cleaning result.

If the at least one mechanical cleaning element is designed as a cylindrical or roller-shaped rotating brush and if a cleaning bath is also used for the cleaning element, then the brush can be partially immersed in the bath when the cleaning apparatus is in operation, with the result that the brush itself is cleaned or rinsed in the cleaning bath constantly during cleaning, which enables a high degree of automation.

With regard to the structural design of the supply of the oxidizing agent, a preferred solution is that the oxidizing agent is supplied via at least one supply line, the at least one supply line being arranged essentially along the longitudinal extension of the at least one cleaning surface of the at least one mechanical cleaning element. The at least one supply line, furthermore, has one, preferably a plurality, of outlet openings oriented toward the at least one cleaning surface for spraying or blowing the oxidizing agent thereon. This design solution is characterized by a simple and quick-to-implement structure and enables the at least one cleaning surface of the at least one mechanical cleaning element to be exposed to oxidizing agent over as much of the entire surface as possible. This design solution is particularly suitable for the use of cylindrical or roller-shaped mechanical cleaning elements, such as cylindrical or roller-shaped sponges or brushes.

Another aspect of the present invention relates to a method for cleaning a metering system, in particular for a dispersion, especially a paint-metering system, the metering system having at least one metering unit with a pump head, the pump head being cleaned by means of a cleaning apparatus with at least one mechanical cleaning element having at least one cleaning surface, in which a microbial attack of the cleaning apparatus is avoided with a method described herein.

The advantages explained above apply accordingly to the advantages of this cleaning method. In particular, the advantages of using the cleaning method in a paint-metering system with a plurality of metering units come into play, since the method according to the invention can effectively prevent the spread of a microbial attack from one metering unit to several or to all other metering units, which always has represented a particular problem in the cleaning methods known in practice.

In terms of the apparatus, the object presented at the beginning is achieved with a cleaning apparatus for a metering system, in particular for a dispersion, especially for a paint-metering system, comprising at least one mechanical cleaning element with at least one cleaning surface and a supply unit for an oxidizing agent for at least temporarily applying an oxidizing agent to the at least one cleaning surface, in which the cleaning apparatus is configured for cleaning the metering system described herein.

Again, what has been said above applies accordingly to the advantages of the apparatus according to the invention.

According to an advantageous embodiment of the cleaning apparatus, the cleaning apparatus comprises a cleaning bath for at least temporarily cleaning the at least one cleaning surface of the at least one mechanical cleaning element when the cleaning apparatus is in operation.

Another aspect of the present invention relates to a metering system for a dispersion, in particular a paint-metering system, comprising a cleaning apparatus described herein.

In addition to the cleaning apparatus according to the invention which can be exposed to oxidizing agent, the metering system according to the invention can also comprise apparatuses for preventing the microbial attack of other parts of the metering system, in particular the dispersion(s) in the container(s). In particular, the metering system can comprise an apparatus, which is used to introduce an oxidizing agent, such as ozone, into one or more of the containers in which the dispersion is stored, as described in international patent application PCT/EP2019/052537 (cf. in particular FIG. 1 and the associated description of the figures in PCT/EP2019/052537). The introduction of oxidizing agent, in particular ozone, into the container(s) of the metering system can be done, for example, with the aid of suitable adapters, as described in international patent application PCT/EP2019/052537 (cf. in particular FIGS. 3, 5, 6, 7a, 7b, 8a, and 8b as well as the associated description of the figures in PCT/EP2019/052537). In this context, express reference is made to the disclosure in international patent application PCT/EP2019/052537. An at least temporary exposure of the cleaning surface of the at least one mechanical cleaning element of the cleaning apparatus, as described herein, combined with an introduction of oxidizing agent into one or more of the containers in which the dispersion is stored, as described in PCT/EP2019/052537, represents an especially preferred embodiment of the present invention.

BRIEF DESCRIPTION OF THE DRAWINGS

The present invention is explained in the following by means of a drawing representing an exemplary embodiment of the invention. The following is shown.

DETAILED DESCRIPTION

Figure 1A:
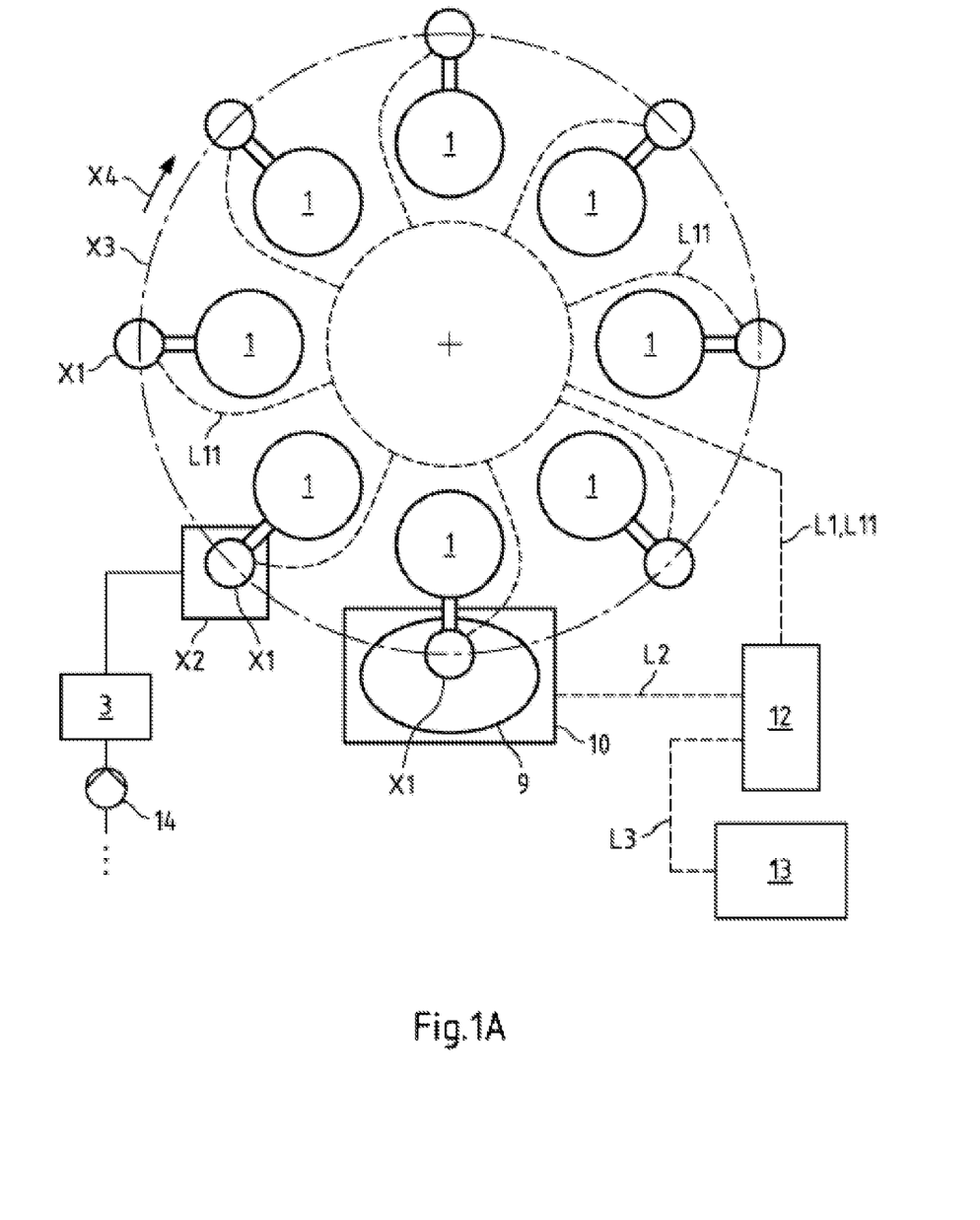
FIG. 1A: a metering system for a dispersion paint with a cleaning apparatus in a schematic plan view.
Figure 1B:
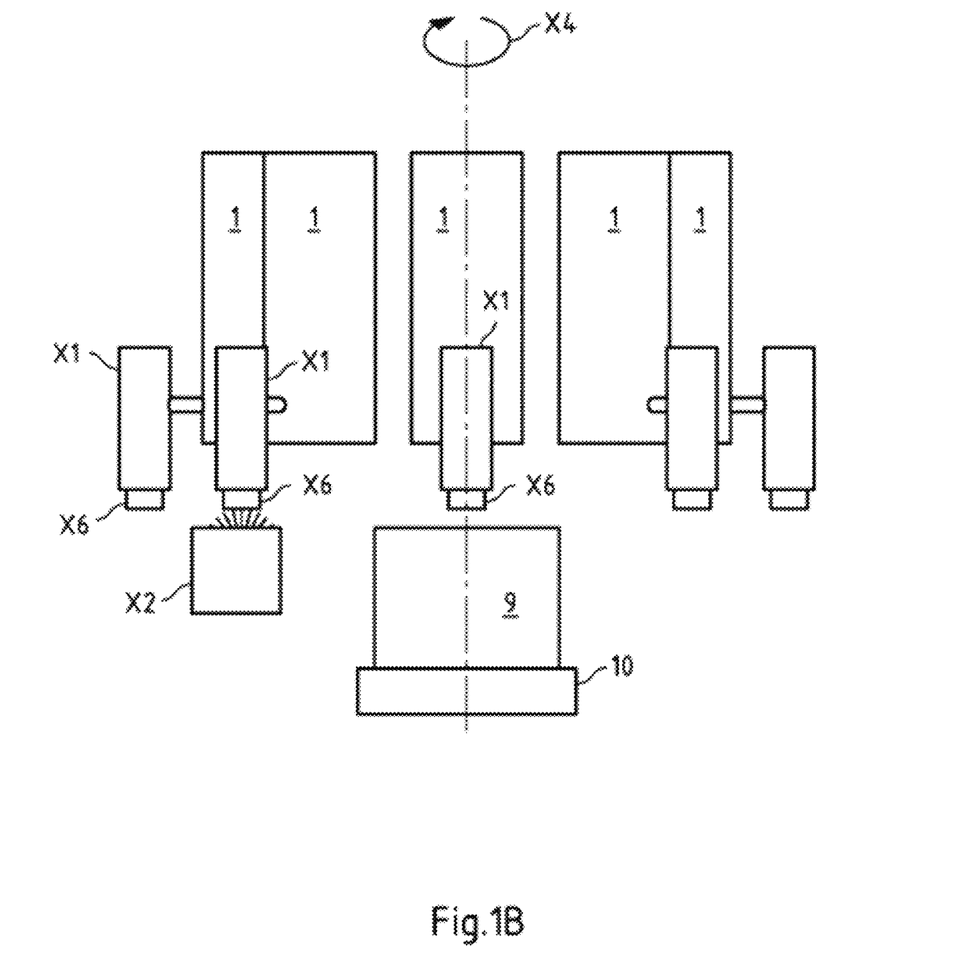
FIG. 1B: the metering system of FIG. 1A in a schematic side view.

FIG. 1 shows a preferred embodiment of a metering system for mixing a dispersion paint with a cleaning apparatus in a schematic plan view. It goes without saying that, in principle, the same structure can also be used for metering and/or mixing other materials.

The metering system of FIG. 1 specifically comprises a plurality of containers 1, in the present case in the manner of a carousel, arranged on a plate X3, which is indicated by a dash-dotted line, each container 1 being connected to a metering unit X1 via a supply line. The drive of the plate X4 is connected to a control computer 12 via a control line L1. Furthermore, the metering units X1 are each connected to the control computer via control lines L11. As can be seen in the plan view of FIG. 1, the metering unit X1 of one of the paint containers 1 is arranged above a receiving container, in this case a bucket 9, so that the dispersion stored in this container 1 can be metered into the bucket 9 via the associated metering unit X1. The bucket 9, in turn, is positioned on a scale 10, which is connected to the control computer 12 via a control line L2. The control computer 12, in turn, is connected to a label printer 13 via a control line L3.

As also shown schematically in FIG. 1A, the cleaning apparatus X2 is connected, via a supply line, to an ozone generator 3, into which air or oxygen, in turn, is introduced via a membrane pump 14. Ozone is generated in the ozone generator 3, for example by means of a corona discharge, which ozone is introduced, via the supply line X24 (only shown schematically in FIG. 1A), into the cleaning apparatus X2 for the purpose of acting on the rotating brush X29.

The metering unit X1, which is adjacent to the metering unit X1 positioned above the bucket 9 in the clockwise direction, is positioned above a cleaning apparatus X2 in such a way that the cleaning apparatus X2, which is described in detail in FIGS. 1B to 4B, can clean the pump head X6 (cf. FIG. 3) of the metering unit X1. As will be explained in more detail below, the cleaning apparatus X2 comprises a mechanical cleaning element in the form of a rotating cylindrical brush X29 with a cylindrical cleaning surface X31 designed as a brush surface, with the aid of which the pump head X6 of each metering unit X1 can be cleaned of paint residue.

When the metering system is in operation, the control computer 12 calculates the proportions of the primary paints stored in the containers 1, after the customer has entered a desired color tone and the desired volume, and controls the drive of the plate X4 in such a way that the metering units X1 of the container 1 with the required basic colors are positioned over the bucket 9, and the calculated amount is dispensed into the bucket 9 so as to obtain the desired color tone in the bucket 9. This is monitored by means of the scales 10 connected to the control computer via the line L2. The drive of the plate X4 is controlled in such a way that it always rotates clockwise. As a result, the pump head X6 of each metering unit X1 involved in the paint mixing process is cleaned by the cleaning apparatus X2 immediately after use and thus cleared of dispersion residue. The appropriate label for the paint mixture is printed via the label printer 13.

Figure 2:
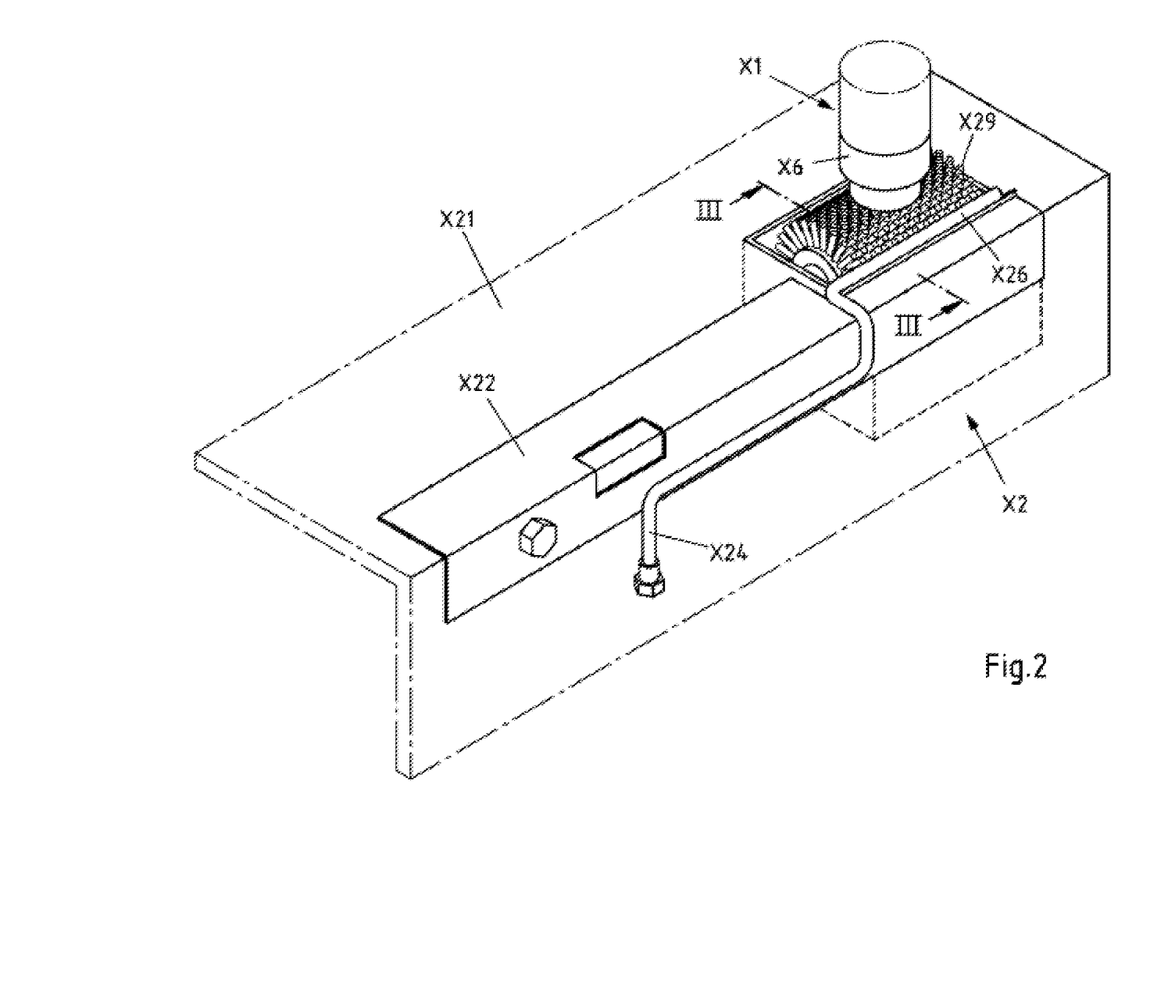
FIG. 2: the cleaning apparatus of the metering system of FIGS. 1A and 1B in a perspective view.
Figure 3:
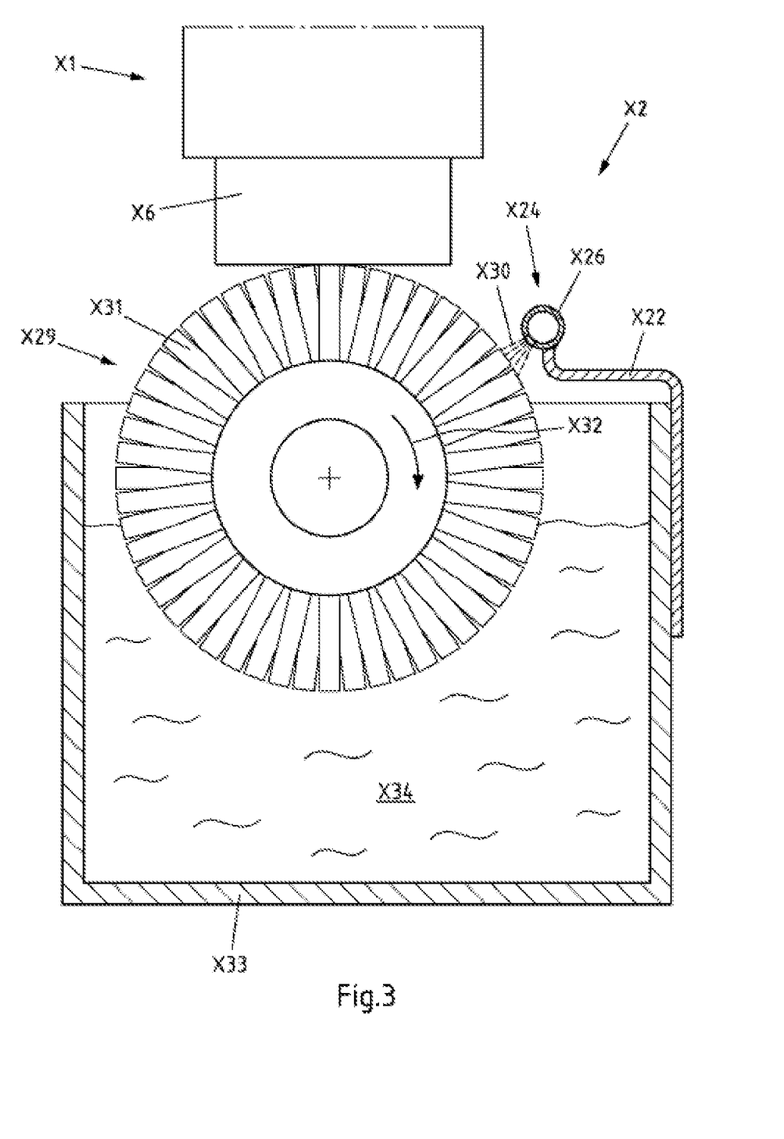
FIG. 3: the cleaning apparatus of FIG. 2 in cross-section according to section line III-III of FIG. 2.

FIGS. 2 and 3 show the cleaning apparatus X2 of the metering system of FIG. 1 in a perspective view and in cross-section according to section line III-III from FIG. 2.

According to FIG. 3, the cleaning apparatus X2 comprises a brush X29 rotating clockwise X32 in the present view as a central element, which brush cleans the pump head X6 of dispersion residue with the bristles of the brush surface X31 arranged at the top during operation, while the bristles at the bottom of the brush X29, which are immersed in a cleaning bath X34, can be cleared of paint residue in the cleaning bath X34. The cleaning bath X34 is formed in the present case by a water bath, which is located in a container X33.

As can be seen in FIGS. 2-3, an ozone-containing gas flow as an oxidizing agent is blown, via the supply line X24, onto the brush X29 by means of a plurality of outlet openings X28 (cf. FIG. 4B) arranged in an outlet region X26 of the supply line (cf. FIG. 4B), in which the gas flow is blown into the brush essentially parallel to the bristles of the brush surface X31, i.e. essentially radially. In the present case, the container X33 of the cleaning bath X34 is connected to a housing X21 via a fastening profile X22.

Figure 4A:
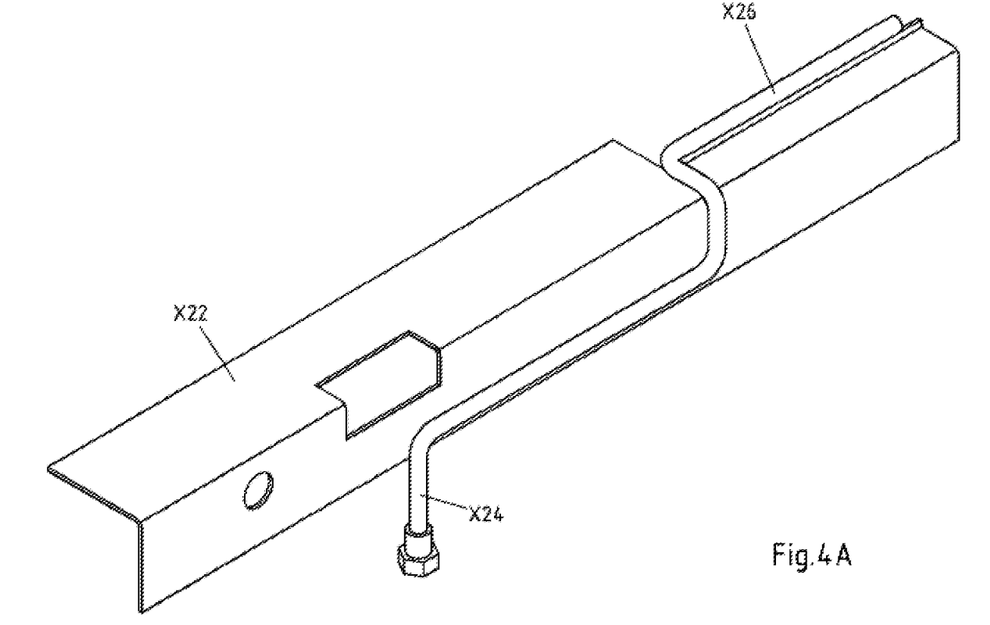
FIG. 4A: the supply of an oxidizing agent of the cleaning apparatus of FIG. 2 in an enlarged perspective view.
Figure 4B:
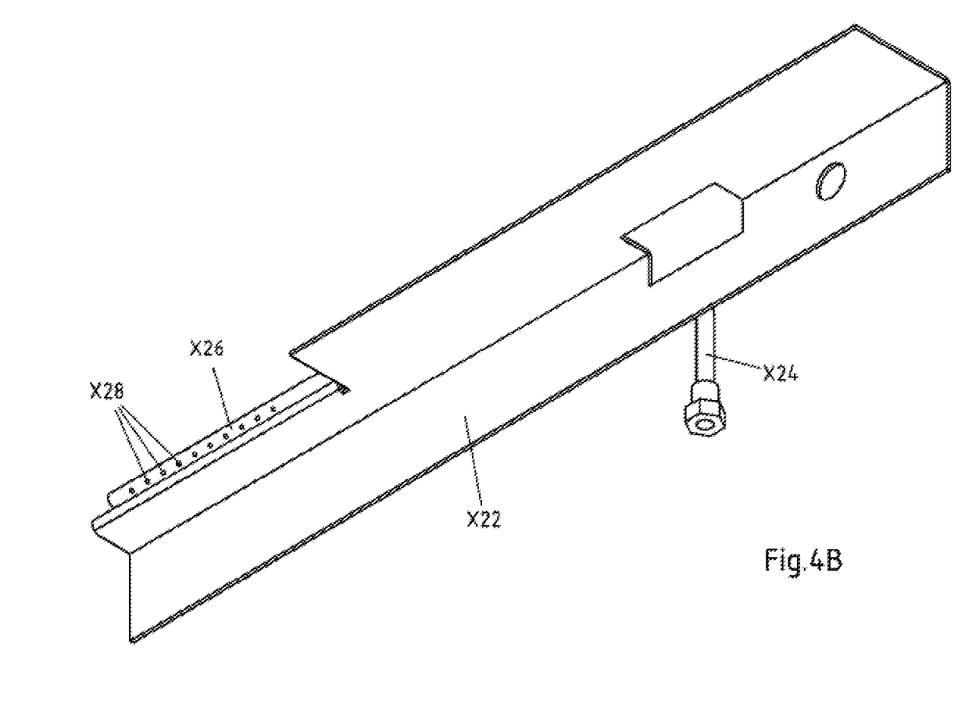
FIG. 4B: the supply of an oxidizing agent of the cleaning apparatus of FIG. 2 in a perspective view which is rotated as relates to FIG. 4A.

The fastening rail X22 together with the supply line X24 for the ozone-containing gas flow is shown again in two perspective views in FIGS. 4A and 4B. In the view in FIG. 4B, the outlet openings X28 for the gas flow are clearly visible in the outlet region X26 of the supply line X24, which outlet region is aligned parallel to the axis of the brush X29 (cf. FIG. 3).

The particular advantage of the cleaning apparatus and the cleaning method is that there is no risk of microbial attack with bacteria and fungi in either the cleaning bath X34 or in the brush X29, as this is effectively prevented by the ozone being blown in as an oxidizing agent by the supply line X24. Accordingly, the method according to the invention for avoiding the microbial attack of the cleaning apparatus X2 has proven to be extremely effective. In addition, the risk of a contamination of other pump heads X6 is minimized by the cleaning apparatus X2, even if it cleans a microbially contaminated pump head X6—and thus corresponding contaminants collect on the bristles of the cylindrical brush surface X31 and in the cleaning bath X34—and then further pump heads X6 are cleaned.

The invention claimed is:

1. A liquid metering system comprising a plurality of containers arranged on a rotatable circular plate comprising a perimeter, each container operably connected to a metering unit arranged along the perimeter, wherein each metering unit is configured to receive a liquid from the container to which it is connected, and wherein each metering unit comprises a pump head configured, in a dispensing position, to dispense the liquid into a receiving container disposed below the rotatable circular plate; and wherein the rotatable circular plate is configured to rotate each metering unit between the dispensing position and a cleaning position; and at the cleaning position, a rotatable brush with bristles is disposed below the rotatable circular plate wherein the rotatable brush with bristles is configured to contact the pump head, wherein a gas comprising ozone is applied essentially radially to a plurality of bristles of the rotatable brush with bristles.

2. The liquid metering system of claim 1 wherein the rotatable brush with bristles is rotatably mounted in a container proximate to the perimeter and partially immersed in a water bath.

3. The liquid metering system of claim 2 wherein a gas comprising ozone is applied radially to a plurality of bristles of the rotatable brush with bristles.

4. The liquid metering system of claim 2, wherein a gas comprising ozone is applied to the bristles by an ozone gas supply line mounted proximate to a plurality of bristles and parallel to an axis of the rotatable brush with bristles, which rotatable brush with bristle is cylindrical.

5. The liquid metering system of claim 4 wherein the ozone gas supply line comprises an outlet region comprising a plurality of apertures out of which the gas comprising ozone exits the supply line.

6. The liquid metering system of claim 5 wherein the plurality of a bristles is treated with the gas comprising ozone, rotated through the water bath, and afterward a allowed to contact a pump head.

* * * * *